(12) United States Patent
Rhee et al.

(10) Patent No.: US 6,402,690 B1
(45) Date of Patent: Jun. 11, 2002

(54) ISOLATING RING SENSOR DESIGN

(75) Inventors: Sokwoo Rhee, Cambridge; Boo-ho Yang, Boston; Haruhiko H. Asada, Lincoln, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/552,185

(22) Filed: Apr. 18, 2000

Related U.S. Application Data

(60) Provisional application No. 60/130,774, filed on Apr. 23, 1999.

(51) Int. Cl.[7] ................................................ A61B 5/00
(52) U.S. Cl. ...................... 600/300; 600/485; 600/500; 600/508; 600/310; 600/549; 600/323; 128/903
(58) Field of Search ................................. 600/300, 301, 600/309–311, 316, 323, 324, 326, 328, 340, 344, 345–348, 355, 361–365, 481–510, 549, 587, 595; 128/897, 898, 903, 920

(56) References Cited

U.S. PATENT DOCUMENTS

| | | |
|---|---|---|
| 3,835,839 A | 9/1974 | Brown |
| 3,878,502 A | 4/1975 | Rochelle |
| 3,972,038 A | 7/1976 | Fletcher et al. |
| 3,972,320 A | 8/1976 | Kalman |
| 4,063,410 A | 12/1977 | Welling |
| 4,396,906 A | 8/1983 | Weaver |
| 4,535,324 A | 8/1985 | Levental |
| 4,799,062 A | 1/1989 | Sanderford, Jr. et al. |
| 4,825,872 A | 5/1989 | Tan et al. |
| 4,827,943 A | 5/1989 | Bornn et al. |
| 4,924,450 A | 5/1990 | Brashear et al. |
| 5,025,793 A * | 6/1991 | Richey et al. ............... 600/485 |
| 5,152,296 A | 10/1992 | Simons |
| 5,285,784 A | 2/1994 | Seeker |
| 5,297,548 A | 3/1994 | Pologe |
| 5,309,916 A | 5/1994 | Hatschek |
| 5,511,546 A | 4/1996 | Hon |
| 5,638,818 A | 6/1997 | Diab et al. |
| 5,661,460 A | 8/1997 | Sallen et al. |
| 5,694,939 A | 12/1997 | Cowings |
| 5,735,800 A * | 4/1998 | Yasakawa et al. ........... 600/503 |
| 5,738,102 A | 4/1998 | Lemelson |
| 5,771,001 A | 6/1998 | Cobb |
| 5,964,701 A | 10/1999 | Asada et al. |
| 6,322,515 B1 * | 11/2001 | Goor et al. .................. 600/485 |

FOREIGN PATENT DOCUMENTS

| | | |
|---|---|---|
| DE | 31 50925 A1 | 6/1983 |
| DE | 3609 913 A1 | 10/1987 |
| EP | 0 467 853 A1 | 7/1991 |
| EP | 0706 776 A1 | 4/1996 |
| EP | 0 724 860 A1 | 8/1996 |
| FR | 1 655 834 A1 | 6/1991 |
| WO | WO 93/16636 | 9/1993 |
| WO | WO 98/17172 | 4/1998 |

* cited by examiner

*Primary Examiner*—Kevin Shaver
*Assistant Examiner*—Michael C Astorino
(74) *Attorney, Agent, or Firm*—Bromberg & Sunstein LLP

(57) ABSTRACT

A monitoring system for monitoring the health status of a patient by performing measurements such as skin temperature, blood flow, blood constituent concentration, and pulse rate at the finger of the patient. The monitoring system has an inner ring proximate to the finger as well as an outer ring, mechanically decoupled from the inner ring, that shields the inner ring from external loads. Measurements are performed in accordance with a protocol that may be preprogrammed, or may be modified on the basis of real-time data or by command from a remotely located medical professional.

20 Claims, 5 Drawing Sheets

EXPERIMENT CONFIGURATION

ISOLATING RING SENSOR DESIGN

The present application claims priority from U.S. Provisional Application Ser. No. 60/130,774, filed Apr. 23, 1999, which is incorporated herein by reference.

TECHNICAL FIELD

The present invention pertains to a device for monitoring the health status of a patient and, more particularly, for isolating such an apparatus from external disturbances.

BACKGROUND OF THE INVENTION

The present invention is an improvement upon finger-ring sensors such as those described in U.S. Pat. No. 5,964,701, issued Oct. 12, 1999, which incorporated herein by reference.

One of the most difficult problems in implementing a sensor that may be worn on the body is the issue of eliminating signal artifacts due to motion of, or forces exerted upon, the sensor. A further problem is the inflexibility of preprogrammed operating protocols.

SUMMARY OF THE INVENTION

In accordance with preferred embodiment of the invention, there is provided a monitoring system for monitoring the health status of a patient. The monitoring system has an inner ring characterized by a first mass. The inner ring is proximate to a finger of the patient and has at least one sensor coupled to the inner ring for providing a signal based on at least one of skin temperature, blood flow, blood constituent concentration, and pulse rate of the patient. The monitoring system also has an outer ring characterized by a second mass. The outer ring is coupled to the finger of the patient. The monitoring system has an electronics module disposed on the outer ring for processing the signal provided by the sensor and a flexible electrical coupling for conveying the signal from the sensor to the electronics module in such a manner as to maintain mechanical decoupling of the inner and outer rings.

In accordance with further embodiments of the invention, the pressure of the inner ring against the finger of the patient may be adjustable within a specified range, including by means of a material having a stiffness that is a nonlinear function of extension. The monitoring system may also have a light source and a detector for monitoring a characteristic of arterial blood flow within the finger, and a control loop for regulating the intensity of light emitted by the light source. Regulation may be in response to a ratio of signal to noise in the detector or to a signal generated by the temperature sensor.

In accordance with yet further embodiments of the invention, a health monitoring system may be provided that has at least one sensor coupled to a ring proximate to a finger of the patient for providing a signal based on at least one of skin temperature, blood flow, blood constituent concentration, and pulse rate of the patient, and an electronics module disposed on the ring for processing the signal provided by the sensor, wherein the electronic module includes a protocol scheduler for specifying a schedule of physiological measurements. The monitoring system may have a transponder for transmitting physiological data based on the sensor signal to a remote station unit and a receiver for receiving protocol scheduling commands from the remote station unit.

BRIEF DESCRIPTION OF THE DRAWINGS

The invention will more readily be understood by reference to the following description taken with the accompanying drawings in which:

FIG. 1b illustrates the effect of an external force on the isolating ring sensor of FIG. 1a;

FIG. 2 depicts a perspective view of an embodiment of the ring sensor device of FIG. 1a;

DETAILED DESCRIPTION OF PREFERRED EMBODIMENTS

Figure 1A:
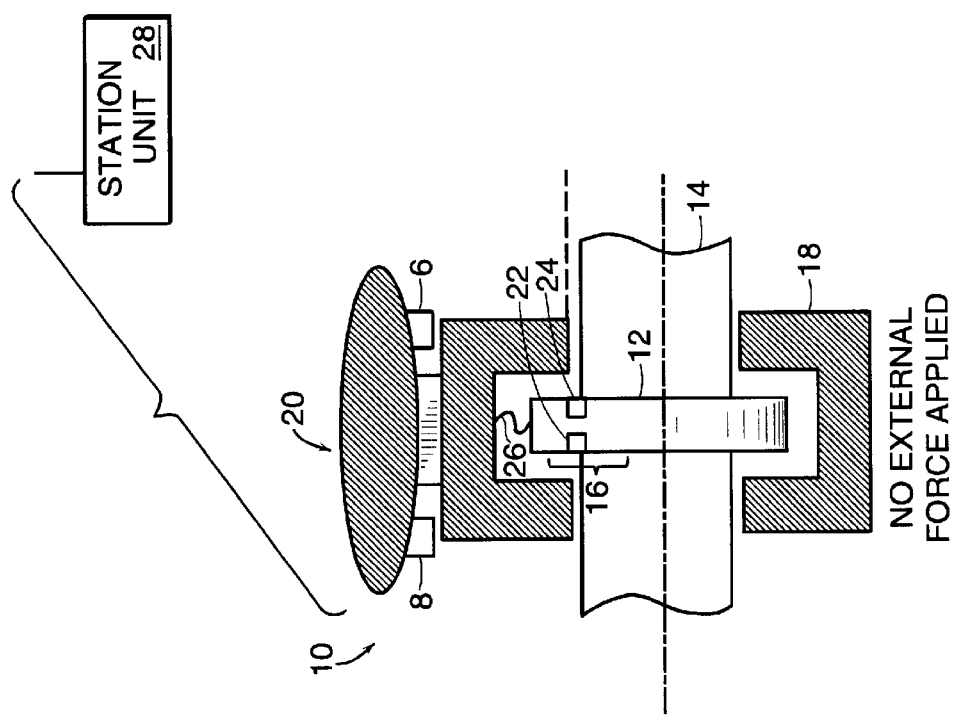
FIG. 1a is a cross-sectional diagram of an isolating ring sensor design in accordance with preferred embodiments of the present invention.

Embodiments of the present invention provide improvements upon finger-ring sensors of the kind described in U.S. Pat. No. 5,964,701, and may also be applied to other sensors worn on the body for monitoring any of a variety of physiological parameters, including, without limitation, skin temperature, electrical impedance, pulse, blood constituent concentration, and/or blood flow. In accordance with preferred embodiments of the invention, sensor data is transmitted to a computer through a wireless communication link and the patient status is analyzed continually and remotely. Any trait of abnormal health status and possible accidents may be detected by analyzing the sensor data. A sensor worn as a finger ring sensor has particular advantages such as that such a sensor may be worn by the patient at all times, hence the health status may be monitored 24 hours a day. For purposes of the present description, the sensor will be referred to, without limitation, as a ring sensor, and the sensing modality, again without limitation, will be described in terms of a photoplethysmographic device for measuring a pulse using optical elements such as infrared light-emitting diodes (LEDs) and photodiodes.

In a preferred embodiment of the invention, the ring sensor is a miniaturized telemetered ambulatory monitoring device in a ring configuration that combines the technology of pulse oximetry with microelectronics and wireless communication technologies. This device optically captures the pulsation and the oxygen saturation of the arterial blood flow of the patient and transmits the signals to a personal computer in a wireless manner. The light emitted from LED traverses human-tissue, and reaches the photodetector, with some of the photons absorbed by tissue including the blood. Since the near infrared (NIR) absorption coefficient of blood exceeds that of the other intervening tissue, the intensity of received light depends on the amount of the blood in the path through the tissue. As a result, when the digital arteries and the capillaries in the finger expand by the pumping activity of the heart, the intensity of light received by the detector decreases. Conversely, the measured light intensity becomes higher when the arteries and the capillaries contract. Such a ring sensor can be worn by the patient twenty-four hours a day at home. Real-time, continuous monitoring with the ring sensor allows not only for emergency detection of an abrupt change of the patient health condition but also for long-term monitoring of vital signs of otherwise difficult and noncompliant patients such as demented elderly people.

Sensors such as the ring sensor, however, are inevitably susceptible to a variety of motion and ambient light artifacts.

For example, in a highly accelerated motion of the patient, the inertia may cause the optical sensor unit to move or slide on the skin surface, and, as a result, the optical sensor measurement may be distorted or even ruined completely. Even a static external force may cause a similar distortion of the measurement due to the relative displacement of the sensor to the finger. Additionally, ambient light may be another major source of measurement artifacts. These kinds of external disturbances can seriously degrade the quality of measurement of the ring sensor. The optical method of measuring pulse is particularly prone to external disturbances, both mechanical and optical. As the signal detected by the optical sensor is amplified thousands of times, any small disturbance on the sensor will result in significant change of the amplified signed and eventually degrade the measurement.

Referring now to FIG. 1a, a ring sensor, denoted generally by numeral 10 is shown in cross-section. An inner ring 12, proximate to a finger 14 of the subject, includes a sensor unit, denoted generally by numeral 16. Inner ring 12, and thus sensor unit 16, are decoupled from most of the inertia of the device. The decoupling may be achieved, in preferred embodiments of the invention, by having two rings, namely inner ring 12 and outer ring 18, which are mechanically independent to each other. By putting the optical sensor unit 16 on one of the rings while a circuit board and battery module 20 is on the other ring, it is possible to protect sensor unit 16 from the influence of the most of any inertia force to which the ring 10 is subjected.

The problem caused by external static forces can also be solved by same approach. The ring device 10 comprises two rings, with a first ring 12 enclosed in the second outer ring 18. Inner ring 12 floats inside outer ring 18 so that static displacement of the outer ring 18 does not substantially influence inner ring 12. The problem of ambient light can be also alleviated by this design since outer ring 18 works as an optical seal for sensor unit 16 on the inner ring 12.

In accordance with preferred embodiments of the invention, inner ring 12 is basically a thin band that carries optical sensor unit 16 which, in turn, includes one or more LEDs 22 and one or more photodiodes 24. Inner ring 12 is made of light material such as plastic or acrylic, or even a rubber band. A rubber or latex band is preferable in that it is flexible and compliant. From the analysis of finger models, it has been found that giving a certain pressure on the optical sensor on the skin may increase the amplitude of the measured signal, resulting in a higher signal to noise ratio. Additionally, using a compliant material for the inner ring may advantageously contribute to holding the finger firmly.

The second part of ring device 10 is the outer ring 18 that carries the circuit board and battery module 20. Additionally, module 20 may include a radio-frequency or other transponder or transmitter for transmitting signals conveying physiological data to a station unit 28, either elsewhere on the person of the patient or in the vicinity-of the patient. Second part 18 is made of a stiffer material such as metal or PVC so that it can sustain the circuit board and the batteries. It also works as a mechanical shelter against external forces. First part 12 is put into the second part 18 such that the first part 12 can float inside the second part 18. Sensor unit 16 is mechanically coupled to the first part 12 and is electrically connected to the circuit board 20 on the second part 18 by means of a few flexible, thin wires 26 that are long enough that the rotation of outer ring 18 does not substantially influence the inner ring 12. Wires 26 are the only connection between the first part 12 and the second part 18. With this configuration, the first part carrying the sensor unit is virtually de-coupled from the movement of the second part, and unconstrained by the influence of the movement of the second part.

Figure 1B:
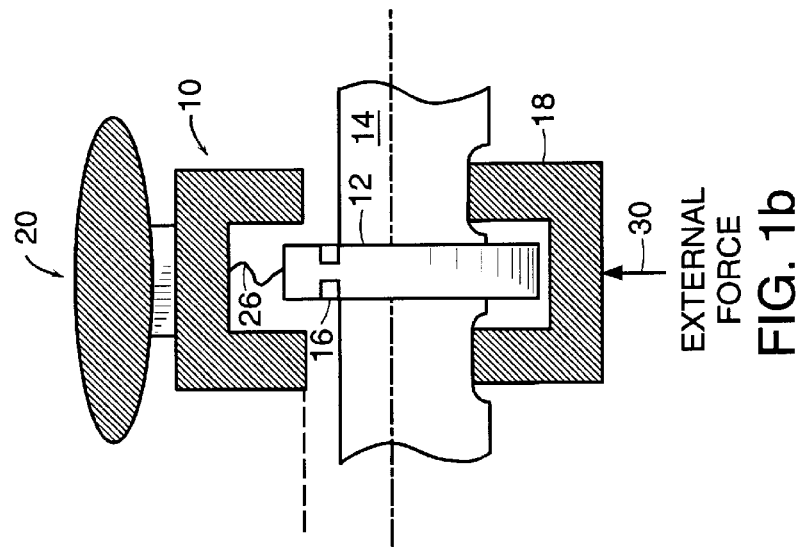

FIG. 1b illustrates the effect of an external force applied in direction 30 on device 10. When an external force is applied to outer ring 18, the relative position of the inner ring 12 to the outer ring 18 changes, however the relative position of the finger 14 to the sensor unit 16 that is attached on the inner ring 12 does not change. It is preferred that the wires 26 that connect the circuit board 20 and the sensor unit 16 electrically be thin and long enough that when the outer ring 18 rotates by any kind of external torque, the inner ring 12 does not rotate substantially although the outer ring 18 may rotate to some extent.

In preferred embodiments of the invention, the miniaturized sensor unit 16 is attached on the internal ring 12 whose mass is almost negligible with respect to the total mass of the device. Typically the ratio of the mass of the outer ring to the mass of the inner ring is at least an order of magnitude. Sensor unit 16 preferably includes a small circuit board (5 mm×5 mm×0.8 mm) that contains two light emitting photodiodes and a photodetector, although other embodiments such as an integrated optical unit are within the scope of the present invention. The main circuit board and batteries comprising module 20 are relatively heavy and bulky sit on the external ring 18 which may also be referred to as a housing. The main circuitry is composed of many small element, which may be of surface mount style or bare die form. Resistors and capacitors are either wire-bonded or glued with conducting epoxy. Integrated circuits may be in die forms and wire-bonded on gold pads on the circuit board. Even though small and light components are used, the total mass of this circuit board is not negligible. In addition. button type batteries used for providing power to the circuit have relatively large mass. In a preferred embodiment of the invention, these components sit on the surface of the outer ring.

Inner ring 12 and the outer ring 18 are connected only by a few wires 26 that are flexible and thin. As a result, the inner ring and the outer ring are virtually isolated mechanically. The outer ring is subject to external forces including direct forces and inertial forces, and it may move or rotate around the finger. However, the inner ring is not substantially influenced by the movement of the outer ring. Moreover, the inner ring floats inside the outer ring. When a person wears the device, both inner ring 12 and outer ring 18 are worn simultaneously, but there is no direct mechanical connection between the two rings except a few thin wires 26 for signal exchange. Thus, any external force applied to the device applies substantially only to the outer ring, and the force is sustained mostly by the parts of the outer ring that are in contact with the finger, The external force-does not substantially influence the contact point between the finger and the internal ring since the two rings are virtually de-coupled. As a result, the measurement from the sensor unit can be kept stable even in the presence of external forces applied to the outer ring.

The isolating ring sensor, in accordance with embodiments of the present invention, may provide the additional advantage of optical isolation since outer ring 18 may serve to block the penetration of ambient light such that the sensor measurement is not influenced significantly by such light.

The pressure with which inner ring 12 is held against finger 14 is known to affect the level of signal in the case of certain measurements. For example, pressure on the outside of blood vessels reduces the stiffness of blood vessel walls, thereby increasing the amplitude of pulse measurement signals, for example. On the other hand, a trade-off exists in that pressure must, not be increased to such an extent as to occlude the free flow of blood within the vessel. Pressures for sensor ring applications have been found advantageously to lie in the range of 10–30 mm Hg. In accordance with an embodiment of the invention, a preferable nonlinear characteristic of tension in ring 12 as a function of extension of the ring is provided by fashioning the ring from an elastomer. In particular, it is desirable that the tension saturate with extension. A preferable material for providing that property is a elastomeric weave such as used in the elastic bands of clothing.

Other factors effect blood flow in the extremities of a mammal, and, more particularly in the finger of a human subject. One such factor is low ambient temperature which causes a reduction in blood flow in the extremities. To compensate for temperature effects, in accordance with an embodiment of the invention, the intensity of light emitted by LED 22 is increased to maintain an acceptable level of signal-to-noise. To that end, a temperature sensor 8 may be provided as part of circuitry 20 to allow for automatic compensation of LED intensity. Alternatively, in accordance with further embodiments of the invention, a signal-to-noise level ratio may be specified, either in hardware or in software, and the LED level may be adjusted by a control loop to maintain the specified ratio or to optimize the signal level within specified constraints which may include power utilization, for example.

Figure 2:
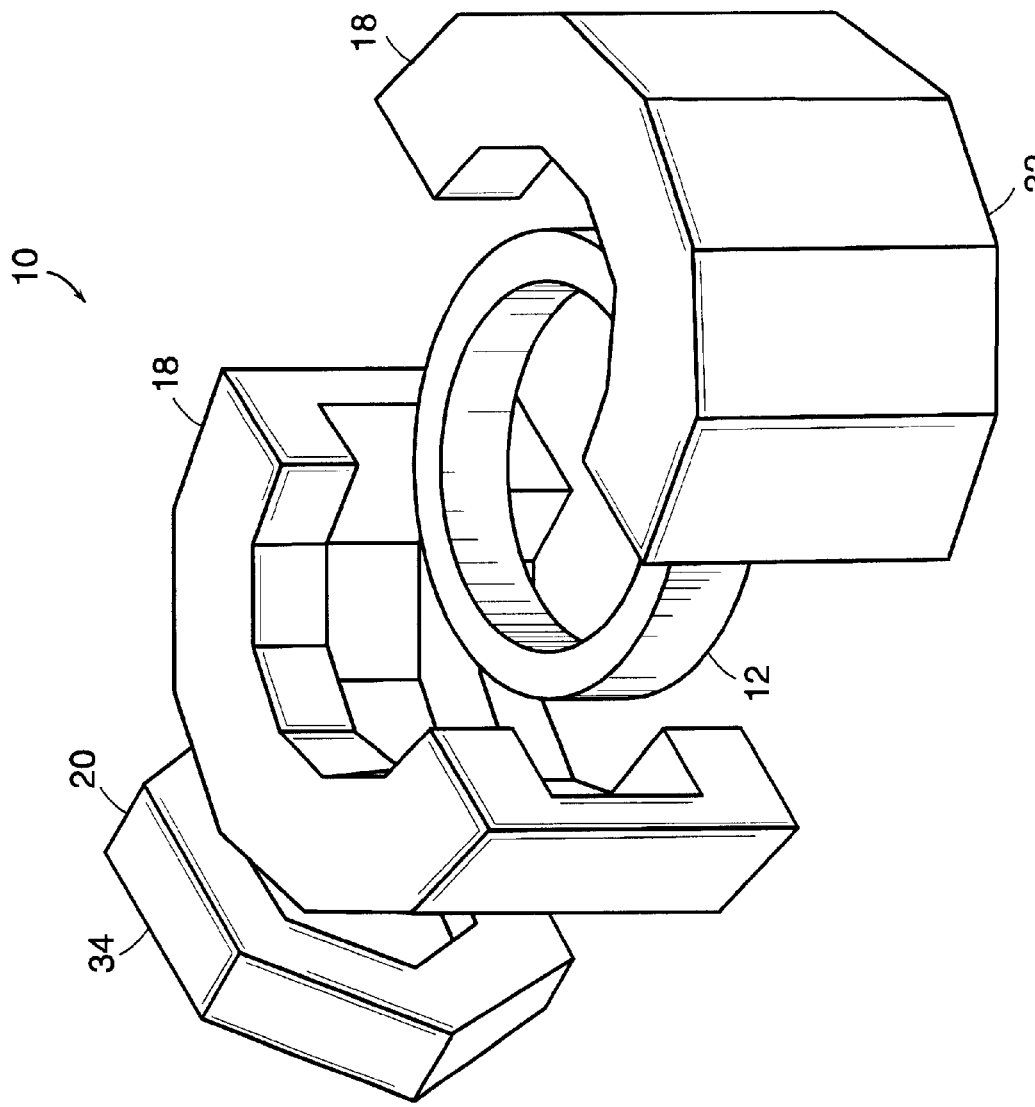

FIG. 2 depicts a perspective view of ring sensor device 10, in accordance with a preferred embodiment of the invention. Outer ring 18 is divided into two pieces 32 and 34 for ease of wearing by the patient. Module 20 containing the signal processing electronics and transmitter is part of outer ring piece 34.

Figure 3:
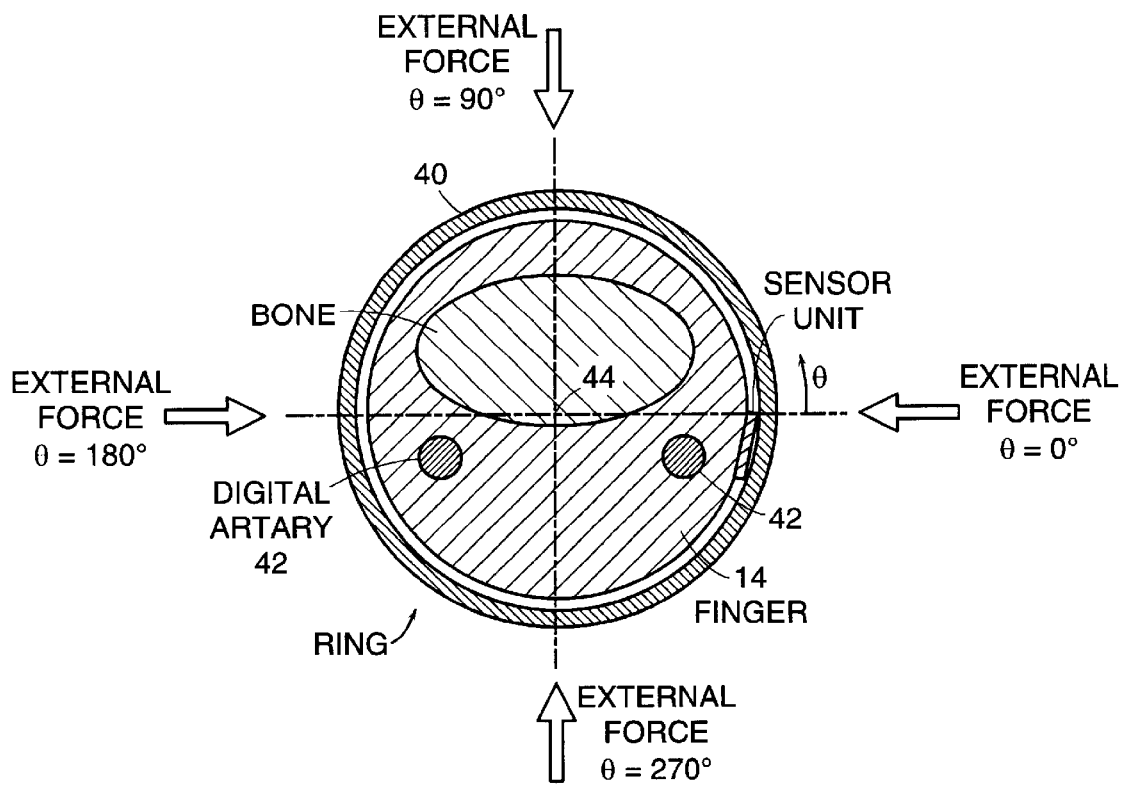
FIG. 3 shows an experimental configuration, in axial cross-section, for evaluating the operation of an isolating ring sensor in accordance with an embodiment of the present invention.

To verify new designs in accordance with an embodiment of the present invention, the measurement obtained from the new dual-ring sensor was compared with that of an old ring sensor. The old ring sensor uses just a simple ring made out of aluminum, which is only one piece. The circuit board is attached on the outer surface of the ring and the sensor unit is attached inner surface of the same ring. Referring now to FIG. 3, an experiment was conducted giving an external static force on the ring 40 at various positions. Digital arteries 42 are shown for angular orientation about axis 44 of finger 14.

Figure 4:
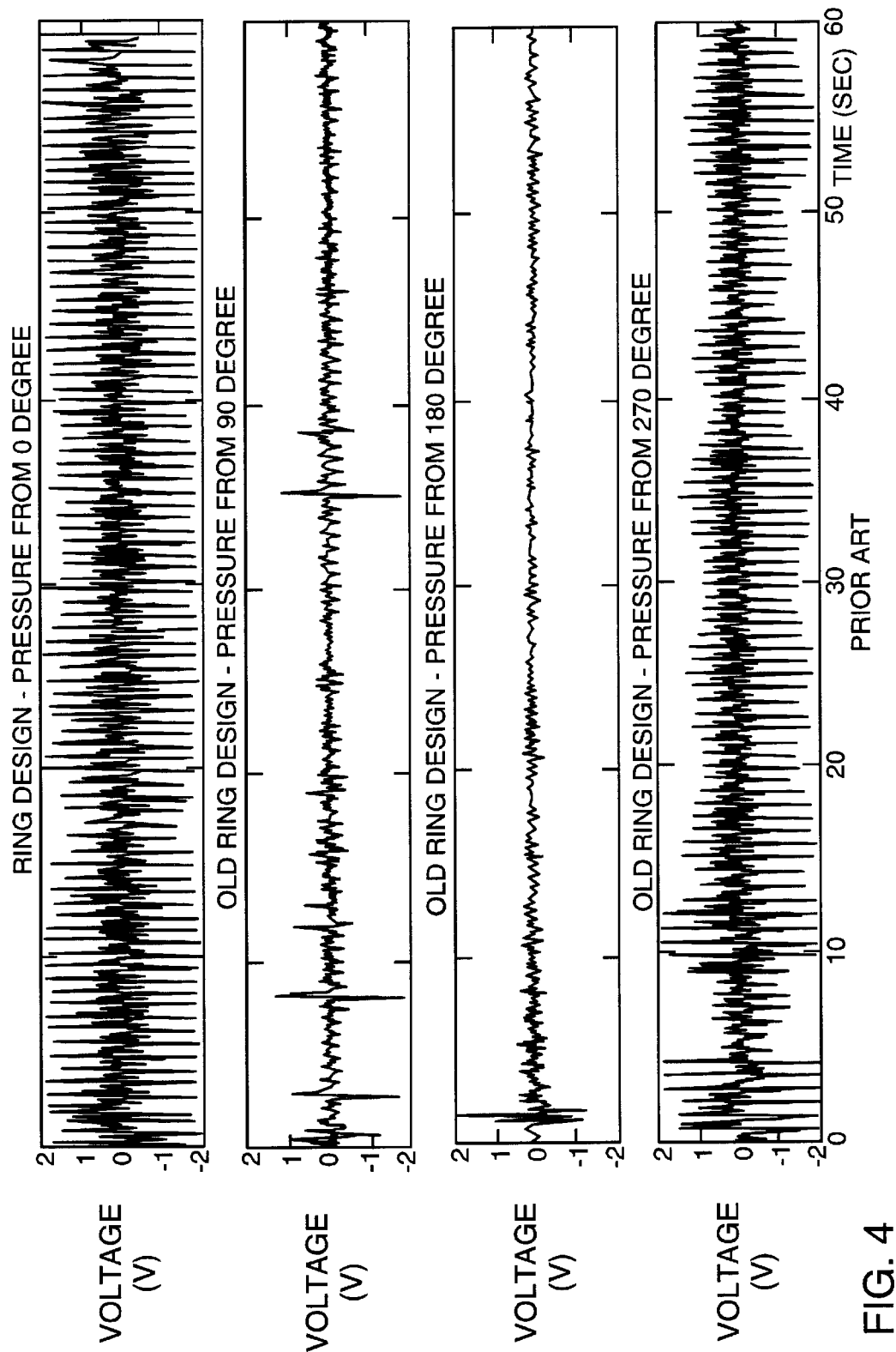
FIG. 4 shows the response of a prior art ring sensor in the face of applied external forces.

Initially, an external pressure was applied on the point of angle θ=0°, and the corresponding photoplethysmograph was measured. The same experiments were conducted with θ=90°, θ=180°, and θ=270°, respectively. The photoplethysmographs from the experiments of the plain (old) ring sensor are shown in FIG. 4, and the results of the new ring are shown in FIG. 5.

In the case of the old ring composed of one piece, the measurement varied significantly as a function of the external forces. With an external force at an angle of θ=0° or 270°, the photoplethysmograph is clear with large amplitude. It is known from analysis of finger models that the signal becomes stronger with a certain pressure on the sensor unit. In the experiment with an external force at 0° or 270°, the amplitude of signal is actually larger than the case with no external force due to the pressure applied on the sensor unit. However, when the external force is applied at 90°, the amplitude of the signal is significantly reduced and the pulses are hard to detect. In this configuration, the pressure applied on the sensor unit is almost zero, and even a small air gap can exists between the optical sensor and the skin, which will seriously degrade the measurement. In the case of θ=180°, the air gap becomes even larger and we can hardly recognize the pulses. Actually this is the worst configuration among the four cases.

Figure 5:
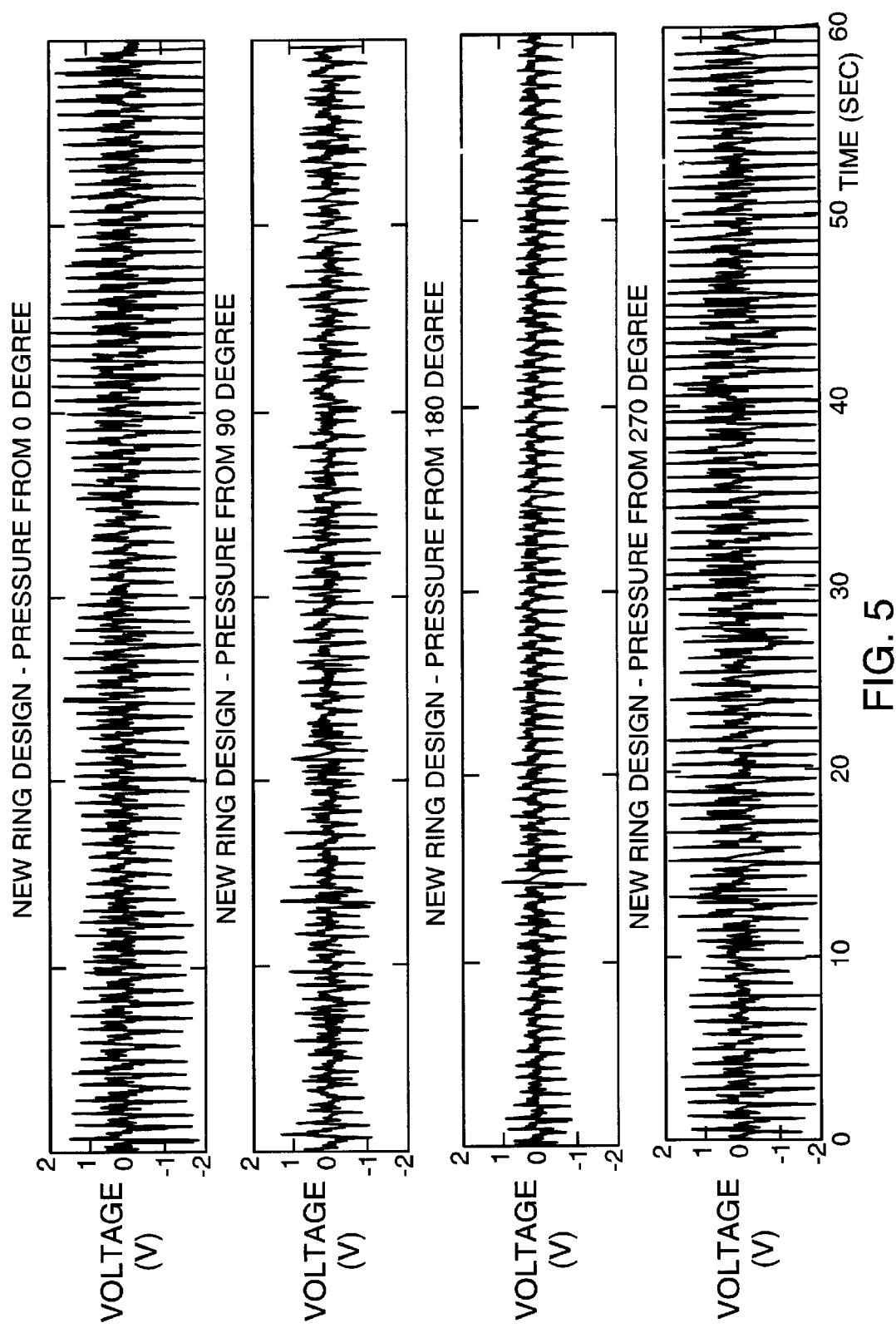
FIG. 5 shows the response of an isolating ring sensor, in accordance with an embodiment of the present invention, in the face of applied external forces.

Referring now to FIG. 5, the photoplethysmographs graphs of a new ring sensor, in accordance with a preferred embodiment of the present invention, show much better results. Because of the reason explained above, the signal is most clear and the amplitude is large with θ=0° or 270°. However, even with an external force applied at θ=90° or 180°, the photoplethysmographic signal is still clear and it is not difficult to identify the pulses. Even at the worst configuration which is θ=180°, the amplitude of signal is relatively small, but is clearly reflecting the human pulse to the extent that is enough to identify the pulse. With this new ring design, there exists no air gap between the optical sensor and the skin even though the outer ring will move from its original position significantly.

The ring sensor apparatus described herein may be operated, in accordance with embodiments of the invention, in a variety of modes. It is recognized that there are inherent trade-offs between accuracy of measuring any physiological parameters and power consumption by the sensor electronics and thus battery charge lifetime. Under some episodic conditions, frequent and accurate monitoring of vital signs may be essential, such as if the patient is undergoing some cardiac distress. Under routine conditions, however, less frequent monitoring will allow for longer operation between battery maintenance operations.

Therefore, various flexible contingent measurement protocols may be provided. For example, a feedback mode provides for modification of the measurement schedule based on real time data. A protocol scheduler 6 (shown in FIG. 1a) is provided, in software or hardware, either on board the ring or at remote station unit 28, to initiate a specified time series of scheduled physiological measurements. Protocol scheduler 6 may be responsive to a command packet uploaded to the ring from a remotely located medical professional or may respond to variations in locally monitored signal-to-noise or to monitored physiological parameters that are programmed to cause a modification of the measurement protocol.

In accordance with an alternate embodiment of the invention, protocol scheduler 6 provides a medical professional at station unit 28 with a menu of physiological monitoring protocols and allows, via bidirectional communications with the sensor ring, for selection by the medical professional of a preferred mode of vital sign measurement.

The described embodiments of the invention are intended to be merely exemplary and numerous variations and modifications will be apparent to those skilled in the art. All such variations and modifications are intended to be within the scope of the present invention as defined in the appended claims.

We claim:

1. A monitoring system for monitoring the health status of a patient, the monitoring system comprising:
   a. an inner ring characterized by a first mass, the inner ring adapted to be proximate to a finger of the patient;
   b. at least one sensor coupled to the inner ring for providing a signal based on at least one of skin temperature, blood flow, blood constituent concentration, and pulse rate of the patient; and
   c. an outer ring characterized by a second mass, the outer ring adapted to be coupled to the finger of the patient substantially externally to the inner ring, the second mass being larger than the first mass, such that the outer ring shields the inner ring from any external loads.

2. A monitoring system according to claim 1, wherein the outer ring further shields the inner ring from ambient light.

3. A monitoring system according to claim 1, wherein the outer ring shields the inner ring from inertial loads.

4. A monitoring system according to claim 1, wherein the outer ring further shields the inner ring from static external forces.

5. A monitoring system according to claim 1, further comprising a flexible electrical coupling for conveying the signal from the sensor to an electronics module in such a manner as to maintain mechanical decoupling of the inner and outer rings.

6. A monitoring system according to claim 1, wherein the pressure of the inner ring against the finger of the patient is adjustable within a specified range.

7. A monitoring system according to claim 1, wherein the pressure of the inner ring against the finger of the patient is within the range of 10–30 mm Hg.

8. A monitoring system according to claim 1, wherein the pressure of the inner ring against the finger of the patient is maintained by a material having a stiffness that is a nonlinear function of extension.

9. A monitoring system according to claim 1, wherein the pressure of the inner ring against the finger of the patient is maintained by an elastomer.

10. A monitoring system according to claim 1, further including a light source and a detector for monitoring a characteristic of arterial blood flow within the finger.

11. A monitoring system according to claim 10, wherein the light source is a light-emitting diode.

12. A monitoring system according to claim 10, further including a control loop for regulating the intensity of light emitted by the light source.

13. A monitoring system according to claim 12, wherein the control loop regulates the intensity of light emitted by the light source in response to a ratio of signal to noise in the detector.

14. A monitoring system according to claim 12, further including a temperature sensor for generating a signal such that the control loop regulates the intensity of light emitted by the light source in response to the signal generated by the temperature sensor.

15. A monitoring system for monitoring the health status of a patient, comprising:
   a. an inner ring characterized by a first mass, the inner ring adapted to be proximate to a finger of the patient;
   b. at least one sensor coupled to tee inner ring for providing a signal based on at least one of skin temperature, blood flow, blood constituent concentration, and pulse rate of the patient;
   c. an outer ring characterized by a second mass, the outer ring adapted to be coupled to the finger of the patient the second mass being larger than the first mass, such that the outer ring shields the inner ring from any external loads;
   d. an electronics module disposed on the outer ring for processing the signal provided by the sensor; and
   e. a flexible electrical coupling for conveying the signal from the sensor to the electronics module in such a manner as to maintain mechanical decoupling of the inner and outer rings.

16. A monitoring system according to claim 15, wherein the flexible electrical coupling includes a plurality of wires.

17. A monitoring system according to claim 15, further comprising:
   a. a transmitter for converting the signal to a wave;
   b. at least one receiver for receiving the wave from the transmitter; and
   c. a controller for analyzing the wave and determining an abnormal health status.

18. A monitoring system according to claim 15, wherein the mass of the outer ring is at least ten times the mass of the inner ring.

19. A monitoring system according to claim 15, wherein the inner ring includes a flexible material.

20. A monitoring system according to claim 19, wherein the tension on the flexible material is a nonlinear function of extension of the flexible material.

* * * * *

UNITED STATES PATENT AND TRADEMARK OFFICE
CERTIFICATE OF CORRECTION

PATENT NO.   : 6,402,690 B1
DATED        : June 11, 2002
INVENTOR(S)  : Sokwoo Rhee et al.

Page 1 of 1

It is certified that error appears in the above-identified patent and that said Letters Patent is hereby corrected as shown below:

Column 8,
Line 8, replace "tee" with -- the --.
Line 13, replace "patient" with -- patient, --.

Signed and Sealed this

Twenty-first Day of January, 2003

JAMES E. ROGAN
*Director of the United States Patent and Trademark Office*